United States Patent [19]

Edwards

[11] 3,939,169
[45] Feb. 17, 1976

[54] ALKYLENE BIS(PYRIDINIUMAREYLENE QUATERNARY SALTS)

[75] Inventor: Philip Neil Edwards, Macclesfield, England

[73] Assignee: Imperial Chemical Industries Limited, London, England

[22] Filed: Dec. 27, 1973

[21] Appl. No.: 428,692

Related U.S. Application Data

[62] Division of Ser. No. 234,648, March 14, 1972, Pat. No. 3,786,058.

[30] Foreign Application Priority Data

Mar. 29, 1971 United Kingdom.................. 8071/71

[52] U.S. Cl......................................... 260/294.8 R
[51] Int. Cl.².................................... C07D 213/40
[58] Field of Search... 260/294.8 R, 295 E, 295 PA, 260/295 A, 295 M-Q, 295.5 A, 295.5 D, 296 D

[56] References Cited
UNITED STATES PATENTS

| | | | |
|---|---|---|---|
| 2,520,902 | 9/1950 | Bersworth...................... | 260/295 R |
| 3,786,058 | 1/1974 | Edwards...................... | 260/294.8 R |

*Primary Examiner*—Henry R. Jiles
*Assistant Examiner*—Robert W. Ramsuer
*Attorney, Agent, or Firm*—Cushman, Darby & Cushman

[57] ABSTRACT

Bis(pyridinium quaternary salts), typically those of the formula:

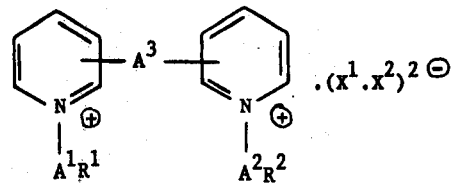

wherein $R^1$ and $R^2$, which may be the same or different, are each an alkyl having 8 to 14 carbon atoms, n-undec-10-yl, 2-n-hexyloxyethyl, 2-(2-butoxyethoxy)ethyl, 3,4-dichlorophenyl, 4-chlorobenzyl, 2,4-dichlorobenzyl or 2-naphthylmethyl; $A^1$ and $A^2$ are each a direct linkage or a linking group of the formula:

$$-CH_2CO.NH-$$

wherein the methylene is joined to the pyridine nitrogen; $(X^1.X^2)^{2\ominus}$ represents two mono-anions or a dianion selected from the group consisting of two halide, methanesulphonate, toluene-p-sulphonate or acetate anions or the sulphate dianion; and $A^3$ is a linking group of the formula:

$$-(CH_2)_n H.CO.NH(CH_2)_y NH.CO.NH(CH_2)_n-$$

wherein $n$ is 0, 1 or 2; and $y$ is 0 or 2 to 6. A process for making these salts, compositions containing them and methods of preventing the growth of, or killing, bacteria by applying one of these salts to a bacterially infected environment, are also disclosed.

6 Claims, No Drawings

ALKYLENE BIS(PYRIDINIUMAREYLENE QUATERNARY SALTS)

This is a division of application Ser. No. 234,648 filed Mar. 14, 1972, now U.S. Pat. No. 3,786,058.

This invention relates to novel pyridine derivatives which possess valuable antibacterial properties and some of which are useful in dental hygiene for inhibiting the formation of dental plaque.

According to the invention there is provided a pyridine derivative of the formula:

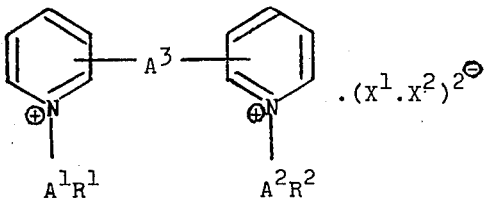

wherein $R^1$ and $R^2$, which may be the same or different, are each an alkyl, alkenyl, alkoxyalkyl, alkoxyalkoxyalkyl, alkanoyloxyalkyl or aryloxyalkyl radical of at least 6 and not more than 14 carbon atoms, a phenyl or naphthyl radical containing 0 to 3 halogen atoms, or an alkyl radical of 1 to 3 carbon atoms which is substituted by a phenyl or naphthyl radical which is itself substituted by 0 to 3 halogen atoms or alkyl or alkoxy radicals of 1 to 6 carbon atoms; $A^1$ and $A^2$, which may be the same or different, are each a direct linkage or a linking group of the formula $-CH_2CO.NH-$ wherein the methylene radical is joined to the pyridine nitrogen atom; $(X^1.X^2)^{2-}$ represents two monoanions or a dianion; and $A^3$ is a linking group selected from 1. $-(CH_2)_z-$
2. $-CH:CH-$
3. $-(CH_2)_nO(CH_2)_n-$, provided that both n's are not 0,
4. $-(CH_2)_n.N(COR^3)(CH_2)_n-$, wherein $R^3$ is an alkyl or aryl radical of up to 10 carbon atoms, and provided that both n's are not 0,
5. $-CH:CH.Y.CH:CH-$
6. $-CO.NHNH.CO(CH_2)_m(CO)_x.NHNH.CO-$
7. $-CO.NHNH.CO.Y.CO.NHNH.CO-$
8. $-CO.N\underset{\diagdown\diagup}{\phantom{XX}}N.CO-$
9. $-CO.NH(CH_2)_yNH.CO-$
10. $-CO.NHCH_2CH_2OCH_2CH_2NH.CO-$
11. $-CO.NH.Y.NH.CO-$
12. $-(CH_2)_n.NH.CO.Y.CO.NH(CH_2)_n-$
13. $-(CH_2)_n.NH.CO.NH.Y.NH.CO.NH(CH_2)_n-$
14. $-(CH_2)_n.NH.CO.NH(CH_2)_yNH.CO.NH(CH_2)_n-$
15. $-(CH_2)_n.NH.CO(CH_2)_m(CO)_x.NH(CH_2)_n-$
16. $-(CH_2)_n.NH.COCH_2OCH_2CO.NH(CH_2)_n-$
17. $-(CH_2)_n.NH.COO.Z.OCO.NH(CH_2)_n-$
18. $-(CH_2)_n.NH.COOCH_2CH_2OCH_2CH_2OCO.NH(CH_2)_n-$
19. $-(CH_2)_{n+1}OCO.NH(CH_2)_yNH.COO(CH_2)_{n+1}-$
20. $-(CH_2)_{n+1}OCO.NH.Y.NH.COO(CH_2)_{n+1}-$
21. $-(CH_2)_{n+1}OCO(CH_2)_yCOO(CH_2)_{n+1}-$
22. $-(CH_2)_{n+1}OCO.Y.COO(CH_2)_{n+1}-$
23. $-(CH_2)_n.NH.CO-$
24. $-NH.COCH:CHCO.NH-$
25. $-NH.CO(CH_2OCH_2)_2CO.NH-$
26. $-NH.CO[O(CH_2)_2]_3OCO.NH-$
27. $-NH.COO(CH_2)_z.NH.CO.NH-$
28. $-NH(CH_2)_mNH-$
29. $-O(CH_2)_mO-$ wherein n is 0, 1 or 2; m is 0 to 12; x is 0 or 1; y is 0 or 2 to 6; z is 2 or 3; Y is a phenylene or naphthylene radical; and Z is a straight- or branched-chain alkylene radical of 2 to 8 carbon atoms.

When $R^1$ and $R^2$ are alkyl, alkenyl, alkoxyalkyl, alkoxyalkoxyalkyl, alkanoyloxyalkyl or aryloxyalkyl radicals, they are preferably straight-chain such radicals, for example n-octyl, n-nonyl, n-decyl, n-undecyl, n-dodecyl, n-tetradecyl, n-undec-10-enyl, 2-n-hexyloxyethyl or 2-(2-butoxyethoxy)ethyl radicals. When $R^1$ and $R^2$ are phenyl or naphthyl radicals containing 0 to 3 halogen atoms, or are alkyl radicals of 1 to 3 carbon atoms substituted by a phenyl or naphthyl radical which is itself substituted by 0 to 3 halogen atoms or alkyl or alkoxy radicals of 1 to 6 carbon atoms, such halogen atoms may be, for example, chlorine or bromine atoms, and the alkyl radical of 1 to 3 carbon atoms may be, for example, the methyl radical, so that $R^1$ and $R^2$ may be, for example, 3,4-dichlorophenyl, 4-chlorobenzyl, 2,4-dichlorobenzyl or 2-naphthylmethyl radicals.

When $(X^1.X^2)^{2-}$ represents two monoanions, suitable anions are, for example, halide anions, for example chloride or bromide anions, anions derived from a carboxylic acid, for example the acetate anion, or anions derived from a sulphonic acid, for example the methanesulphonate or toluene-p-sulphonate anions; and when $(X^1.X^2)^{2-}$ represents a dianion, a suitable anion is, for example, the sulphate or phosphate anion.

It is to be understood that although $(X^1.X^2)^{2-}$ represents two monoanions or a dianion, the corresponding monovalent radicals or atoms are $X^1$ and $X^2$, and the corresponding divalent radical is $(X^1.X^2)$. Thus, for example, $X^1$ and $X^2$ may each be chlorine or bromine atoms, or methanesulphonyl, toluenesulphonyl or acetoxy radicals, and $(X^1.X^2)$ may be, for example, the sulphate divalent radical.

A suitable phenylene or naphthylene radical is, for example, the o-phenylene, m-phenylene, p-phenylene, 1,4-naphthylene, 1,5-naphthylene, 4-methyl-1,2-phenylene, 2,5-dimethyl-1,4-phenylene, 2,5-dimethoxy-1,4-phenylene or 2,4,5,6-tetrachloro-1,3-phenylene radical.

A suitable value for Z is, for example, the ethylene, trimethylene, hexamethylene or 2,2-diethyltrimethylene radical.

Preferred linking groups $A^3$ are those numbered 1, 2, 6, 8, 9, 11, 12, 14, 15, 17, 18, 23, 24, 25, 26, 27, 28 and 29 in the list above, and of these, particular linking groups $A^3$ are:

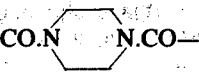

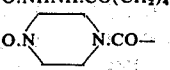

—CO.NH(CH₂)₂₋₆NH.CO— (9, y=2-6)

-continued

—CO.NH　NH.CO— (11, Y=1,2-phenylene)

—CO.NH—⟨⟩—NH.CO— (11, Y=1,4-phenylene)

—NH.CO—⟨⟩—CO.NH— (12, n=0, Y=1,4-phenylene)
—NH.CO.NH(CH₂)₃₋₆NH.CO.NH— (14, n=0, y=3-6)
—CH₂NH.CO.NH(CH₂)₆NH.CO.NHCH₂— (14, n=1, y=6)
—NH.CO.NH— (15, n=0, m=0, x=0)
—NH.COCO.NH— (15, n=0, m=0, x=1)
—NH.CO.NHCH₂— (15, first n=0, second n=1, m=0, x=0)

—CH₂NH.CO.NHCH₂— (15, n=1, m=0, x=0)
—NH.CO(CH₂)₁₋₈CO.NH— (15, n=0, m=1-8, x=1)
—CH₂NH.CO(CH₂)₂₋₄CO.NHCH₂— (15, n=1, m=2-5, x=1)
—NH.COO(C₂₋₇ alkylene)OCO.NH— (17, n=0, Z=C₂₋₇alkylene)
—NH.CO[O(CH₂)₂]₂OCO.NH— (18, n=0)
—NH.CO— (23, n=0)
—CH₂NH.CO— (23, n=1)
—NH.COCH=tCHCO.NH— (24, trans double bond)
—NH.CO(CH₂OCH₂)₂CO.NH— (25)
—NH.CO[O(CH₂)₂]₃OCO.NH— (26)
—NH.COO(CH₂)₂NH.CO.NH— (27, z=2)
—NH(CH₂)₂₋₁₀NH— (28, m=2-10)
—O(CH₂)₄₋₁₀O— (29, m=4-10)

Preferred compounds of the invention are those wherein the radicals —A¹R¹ and —A²R² are the same, and a preferred group of pyridine derivatives of the invention comprises those compounds of the formula I above wherein A¹ and A² are each a direct linkage, R¹ and R² are each the same alkyl or alkenyl radical of 8 to 11 carbon atoms, (X¹.X²)²⁻ represents two bromide, chloride, methanesulphonate, toluene-p-sulphonate or acetate anions, or the sulphate dianion, and A³ is:

—(CH₂)₃—
—CH:CH—
—CO.NH(CH₂)₄₋₆NH.CO—
—NH.CO.NH(CH₂)₃₋₆NH.CO.NH—
—CH₂NH.CO.NH(CH₂)₆NH.CO.NHCH₂—
—NH.CO.NH—
—NH.CO.NHCH₂—
—CH₂NH₂.CO.NHCH₂—
—NH.CO(CH₂)₁₋₈CO.NH—
—NH.COO(CH₂)₂₋₇OCO.NH—
—NH.CO[O(CH₂)₂]₂₋₃OCO.NH—
—CH₂NH.CO—

—NH.COCH=tCHCO.NH—
—NH.CO(CH₂OCH₂)₂CO.NH—
—NH.COO(CH₂)₂NH.CO.NH— or
—O(CH₂)₄₋₁₀O—.

A particularly preferred sub-group within the above group comprises those compounds wherein A¹ and A² are each a direct linkage, R¹ and R² are each an unbranched alkyl radical of 8 to 11 carbon atoms, optionally containing a terminal double bond, (X¹.X²)²⁻ represents two bromide, chloride, methanesulphonate, toluene-p-sulphonate or acetate anions, or the sulphate dianion, and A³ is the trimethylene or ureylene radical or a radical of the formula —NH.CO(CH₂)₃₋₈.CO.NH—, and especially those compounds wherein A³ is linked to the same numbered carbon atom of each pyridine ring.

Particular new pyridine derivatives of the invention are described in Examples 1 to 4, and of these, individual, specially preferred derivatives are 4,4'-trimethylenebis(1-n-decylpyridinium methanesulphonate), (compound 5); 3,3'-ureylenebis(1-n-decylpyridinium methanesulphonate), (compound 25); 3,3'-ureylenebis(1-n-decylpyridinium chloride), (compound 26); 3,3'-glutaramidobis(1-n-decylpyridinium chloride), (compound 78); 3,3'-glutaramidobis(1-n-decylpyridinium methanesulphonate), (compound 79); 3,3'-adipamidobis(1-n-decylpyridinium methanesulphonate), (compound 30); 4,4'-adipamidobis(1-n-decylpyridinium methanesulphonate), (compound 82); 3,3'-pimelamidobis(1-n-decylpyridinium chloride), (compound 86); 3,3'-suberamidobis(1-n-decylpyridinium chloride), (compound 87); 3,3'-subereamidobis(1-n-decylpyridinium methanesulphonate), (compound 88); 3,3'-azelamidobis(1-n-decylpyridinium methanesulphonate), (compound 90); 3,3'-sebacamidobis(1-n-octylpyridinium methanesulphonate), (compound 31); and 3,3'-sebacamidobis(1-n-decylpyridinium methanesulphonate), (compound 32).

According to a further feature of the invention there is provided a process for the manufacture of the novel pyridine derivatives of the invention which comprises:

a. The quaternisation of a pyridine derivative of the formula:

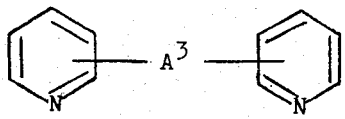 II

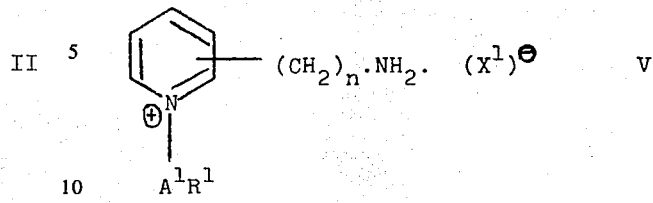 V with a quaternising agent or quaternising agents $(R^1A^1).X^3$, $(R^2A^2).X^4$ or $(R^1A^1)(R^2A^2).(X^3.X^4)$ wherein $A^1$, $A^2$, $A^3$, $R^1$ and $R^2$ have the meanings stated above and $X^3$, $X^4$ and $(X^3.X^4)$ are radicals derived from the acids $HX^3$, $HX^4$ and $H_2(X^3.X^4)$ respectively, which are strong acids; or b. the quaternisation of a pyridine derivative of the formula:

with a suitable mono- or di-carboxylic acid, or a reactive derivative thereof wherein $A^1$, $R^1$, $X^1$ and $n$ have the meanings states above; or d. for those compounds wherein the linking group $A^3$ contains one or two urea linkages, the reaction of an amine of the formula V with a mono- or di-isocyanate, or the reaction of an isocyanate of the formula:

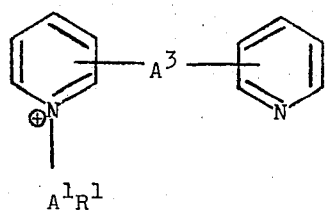 III

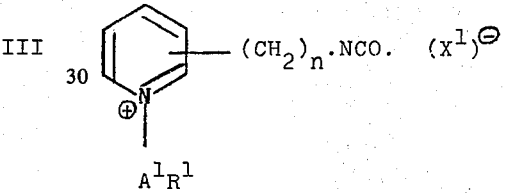 VI with a quaternising agent $(R^2A^2).X^4$, wherein $A^1$, $A^2$, $A^3$, $R^1$, $R^2$, $X^1$ and $X^4$ have the meanings stated above; or c. for those compounds wherein the linking group $A^3$ contains one or two amide linkages, the reaction of a mono-carboxylic acid of the formula:

wherein $A^1$, $R^1$, $X^1$ and $n$ have the meanings stated above, with a suitable monobasic or dibasic compound; or e. for those compounds wherein the linking group $A^3$ contains one urea linkage and which are symmetrical, the reaction of an amino compound of the formula V wherein $A^1$, $R^1$, $X^1$ and $n$ have the meanings stated above, with a carbonyl compound of the formula $(R^4)_2.CO$, wherein $R^4$ is a chlorine atom, a lower alkoxy radical or a phenoxy radical; or f. for those compounds wherein the linking group $A^3$ contains two urethane linkages, the reaction of an amino compound of the formula V with a suitable bis-chloroformate ester, or the reaction of a chloroformate ester of the formula:

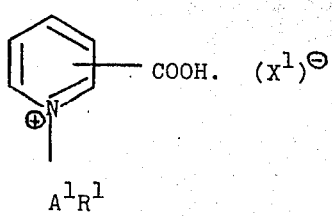 IV

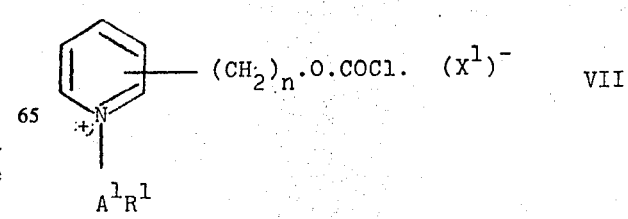 VII or a reactive derivative thereof, with a suitable monobasic or dibasic compound, or the reaction of an amine of the formula:

wherein $A^1$, $R^1$, $X^1$ and $n$ have the meanings stated above, with a suitable dibasic compound; or g. for those compounds wherein the linking group $A^3$ contains two urethane linkages, the reaction of a hydroxy compound of the formula:

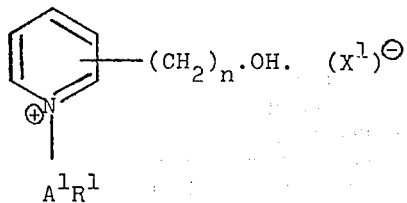
VIII with a suitable di-isocyanate, or the reaction of an isocyanate of the formula:

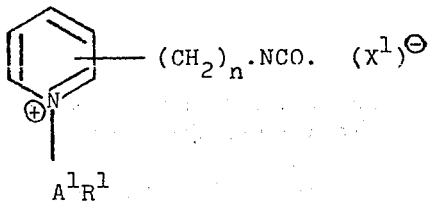
IX with a suitable dihydroxy compound wherein $A^1$, $R^1$, $X^1$ and $n$ have the meanings stated above; or h. for those compounds wherein the linking group $A^3$ contains one or two olefinic linkages, the reaction of an activated methylpyridinium salt of the formula:

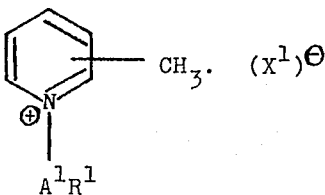
X wherein $A^1$, $R^1$ and $X^1$ have the meanings stated above, with a suitable mono- or di-aldehyde;

whereafter if desired a product thus obtained containing an anion $(X^3)^-$, $(X^4)^-$ or $(X^3.X^4)^{2-}$ is converted to a corresponding compound containing a different anion $(X^1)^-$, $(X^2)^-$ or $(X^1.X^2)^{2-}$ by basification thereof followed by reaction of the basified product with an acid $HX^1$, $HX^2$ or $H_2(X^1.X^2)$ wherein $X^1$, $X^2$, $X^3$ and $X^4$ have the meanings stated above, or by an ion-exchange resin.

The quaternisation process is preferably carried out by heating together the pyridine derivative and quaternising agent, and the inclusion of a solvent, for example nitrobenzene, sulpholane or toluene, is often advantageous in improving the mutual solubilities of the reactants, or to moderate the reaction. The addition of a tertiary amine, for example a hindered tertiary amine such as di-isopropylethylamine is also useful, for removing any acid generated during the reaction.

The processes (c) to (h) for the formation of amide, urea, urethane or olefin linkages may be carried out in generally known manner described in the literature for analogous compounds.

A suitable strong acid $HX^3$, $HX^4$ or $H_2(X^3.X^4)$ has a $pK_a$ value of less than 2, and is, for example, hydrochloric, hydrobromic, methanesulphonic, toluene-p-sulphonic or sulphuric acid.

As stated above, the new compounds of the invention possess valuable antibacterial properties, in that they are effective against a wide range of both Gram-positive and Gramnegative organisms, including strains of, for example, *Pseudomonads* which are resistant to other widely-used antibacterial agents. Further advantages of the preferred compounds of the invention may include, for example, rapid speed of kill, being bactericidal rather than bacteriostatic, not being deactivated by hard water, or having more surface activity. Further, textile materials which have been in contact with the compounds of the invention are not stained by treatment with hypochlorite bleach.

Thus, according to a further feature of the invention, there is provided a composition comprising at least one pyridine derivative of the invention together with an inert diluent or carrier.

The composition of the invention may be a pharmaceutical composition, for example in the form of a lozenge suitable for oral administration, or an ointment, cream, or sterile aqueous or oily solution or suspension for topical use; or it may be a non-pharmaceutical composition, in the form of, for example, a non-sterilised aqueous or oily solution or suspension, or an aerosol, for use as a general, enviromental antiseptic or disinfectant, or a mouthwash, paste, gel or fluid suspension suitable for use in dental hygiene for the inhibition of dental plaque formation.

The composition may contain conventional excipients and carriers, and may be manufactured by the application of conventional techniques.

Preferred pharmaceutical compositions of the invention are lozenges, each containing from 0.1 to 1.0% w/w of a new compound of the invention, and preferred non-pharmaceutical compositions are an aqueous solution suitable for use as an antiseptic and containing from 0.02 to 1.0% w/v of a compound of the invention, an aqueous solution in the form of a concentrate containing from 1% w/w to that percentage which gives a saturated solution of a compound of the invention, or powder or tablets for dissolution in water to give an aqueous solution suitable for use as an antiseptic. Preferred compositions for use in dental hygiene are mouthwashes containing between 0.05% and 0.5% w/v (at user dilution) of a compound of the invention; and toothpastes and dental gels containing between 0.05% and 1.0% w/w, preferably between 0.1% and 0.5% w/w, of a compound of the invention.

The invention is illustrated but not limited by the following Examples:

EXAMPLE 1

General procedure for quaternisation

The pyridine derivative (0.01 mole) and the alkylating agent (0.02–0.1 mole) are heated together, optionally with inclusion of a solvent, e.g. nitrobenzene to improve the mutual solubilities, or to moderate the reaction, and/or a hindered amine, for example di-isopropylethylamine to remove any acid generated during the reaction. The temperature and time of heating are shown for each compound in the Tables, but these are not necessarily optimal conditions and they can usually be varied over wide ranges. The product is crystallised from a suitable solvent and, if required, the anion can be changed by conventional procedures, for example by the use of ion-exchange resins.

$$\underset{A^1R^1}{\overset{\oplus}{\text{Ar}}}-A^3-\underset{A^2R^2}{\overset{\oplus}{\text{Py}}} \cdot (X^1.X^2)^{2\ominus}$$

| No. | $A^1=A^2$ | $R^1=R^2$ | First linkage$^{(a)}$ | $A^{3(b)}$ | Second linkage$^{(c)}$ | $X^1=X^2$ |
|---|---|---|---|---|---|---|
| 1 | — | n-octyl | 4 | —CH₂CH₂— | 4 | Ms$^{(d)}$ |
| 2 | — | n-decyl | 4 | —CH₂CH₂— | 4 | Ms |
| 3 | — | n-dodecyl | 4 | —CH₂CH₂— | 4 | Ms |
| 4 | — | n-octyl | 4 | —(CH₂)₃— | 4 | Ms |
| 5 | — | n-decyl | 4 | —(CH₂)₃— | 4 | Ms |
| 6 | — | n-dodecyl | 4 | —(CH₂)₃— | 4 | Ms |
| 7 | — | n-tetradecyl | 4 | —(CH₂)₃— | 4 | Br |
| 8 | — | n-decyl | 4 | —CH:CH— | 4 | Ms |
| 9 | — | n-undecyl | 4 | —CH:CH— | 4 | Br |
| 10 | — | n-dodecyl | 4 | —CH:CH— | 4 | Ms |
| 11 | —CH₂CONH—$^{(e)}$ | 3,4-dichlorophenyl | 4 | —CH:CH— | 4 | Cl |
| 12 | — | n-octyl | 2 | —CH:CH— | 2 | Ms |
| 13 | — | n-decyl | 2 | —CH:CH— | 2 | Ms |
| 14 | — | n-octyl | 3 | —CH:CH— | 3 | Ms |
| 15 | — | n-decyl | 3 | —CH:CH— | 3 | Ms |
| 16 | — | n-dodecyl | 3 | —CH:CH— | 3 | Ms |
| 17 | — | n-octyl | 3 | —CH:CH— | 4 | Ms |
| 18 | — | n-decyl | 3 | —CH:CH— | 4 | Ms |
| 19 | — | 2-n-hexyloxyethyl | 3 | —CH:CH— | 4 | Ms |
| 20 | — | 4-chlorobenzyl | 3 | —CH:CH— | 4 | Cl |
| 21 | — | 2,4-dichlorobenzyl | 3 | —CH:CH— | 4 | Cl |
| 22 | — | 2-naphthylmethyl | 3 | —CH:CH— | 4 | Br |
| 23 | — | n-decyl | 2 | —CH:CH— | 3 | Ms |
| 24 | — | n-octyl | 3 | —NH.CO.NH— | 3 | Ms |
| 25 | — | n-decyl | 3 | —NH.CO.NH— | 3 | Ms |
| 26 | — | n-decyl | 3 | —NH.CO.NH— | 3 | Cl |
| 27 | — | n-decyl | 3 | —NH.CO.CO.NH— | 3 | Ms |
| 28 | — | n-decyl | 3 | —NH.CO(CH₂)₂CO.NH— | 3 | Ms |
| 29 | — | n-octyl | 3 | —NH.CO(CH₂)₄CO.NH— | 3 | Ms |
| 30 | — | n-decyl | 3 | —NH.CO(CH₂)₄CO.NH— | 3 | Ms |
| 31 | — | n-octyl | 3 | —NH.CO(CH₂)₈CO.NH— | 3 | Ms |
| 32 | — | n-decyl | 3 | —NH.CO(CH₂)₈CO.NH— | 3 | Ms |
| 33 | — | n-decyl | 3 | —CH₂NH.CO.NH.CH₂— | 3 | Br |
| 34 | — | n-decyl | 3 | —CH₂.NH.CO(CH₂)₂CO.NH.CH₂— | 3 | Ms |
| 35 | — | n-decyl | 3 | —CH₂.NH.CO(CH₂)₄CO.NH.CH₂— | 3 | Ms |
| 36 | — | n-octyl | 3 | —NH.CO— | 3 | Ms |
| 37 | — | n-decyl | 3 | —NH.CO— | 3 | Ms |

-continued

| No. | $A^1=A^2$ | $R^1=R^2$ | First linkage[a] | $A^{3[b]}$ | Second linkage[c] | $X^1=X^2$ |
|---|---|---|---|---|---|---|
| 38 | — | n-octyl | 3 | —NH.CO— | 4 | Ms |
| 39 | — | n-decyl | 3 | —NH.CO— | 4 | Ms |
| 40 | — | n-octyl | 3 | —CH$_2$.NH.CO— | 3 | Ms |
| 41 | — | n-decyl | 3 | — CH$_2$.NH.CO— | 3 | Ms |
| 42 | — | n-octyl | 2 | —CH$_2$.NH.CO— | 3 | Ms |
| 43 | — | n-decyl | 2 | —CH$_2$.NH.CO— | 3 | Ms |
| 44 | — | n-octyl | 3 | —CH$_2$.NH.CO— | 4 | Ms |
| 45 | — | n-decyl | 3 | —CH$_2$.NH.CO— | 4 | Ms |
| 46 | — | n-octyl | 2 | —CH$_2$.NH.CO— | 4 | Ms |
| 47 | — | n-decyl | 2 | —CH$_2$.NH.CO— | 4 | Ms |
| 48 | — | n-octyl | 4 | —CO.NH(CH$_2$)$_2$NH.CO— | 4 | Ms |
| 49 | — | n-decyl | 4 | —CO.NH(CH$_2$)$_2$NH.CO— | 4 | Ms |
| 50 | — | n-decyl | 4 | —CO.NH(CH$_2$)$_6$NH.CO— | 4 | Ms |

[a]linkage of left hand pyridine ring to A$^3$ in the formula as written at the head of the table.
[b]where A$^3$ is not symmetrical, it should be read as from left to right in the formula at the head of the table.
[c]linkage of A$^3$ to right hand pyridine ring in the formula as written at the head of the table.
[d]Ms=methanesulphonate.
[e]the methylene group is attached to the pyridine nitrogen atom, and the NH group is attached to R.

| No. | Temperature (°C.) | Time (minutes) | Additive | M.p.(°C.) |
|---|---|---|---|---|
| 1 | 120 | 5 | — | 162–165 |
| 2 | 120 | 5 | — | 190–192 |
| 3 | 155 | 10 | — | 265–267 (decomposition) |
| 4 | 120 | 10 | — | 61–63 |
| 5 | 120 | 10 | — | 78–81 |
| 6 | 120 | 15 | — | 87–89 |
| 7 | 130 | 15 | — | 83–86 |
| 8 | 130 | 30 | — | 201–205 |
| 9 | 130 | 10 | — | 315–317 |
| 10 | 130 | 10 | — | 236–238 |
| 11 | 140 | 1 | — | 255 (decomposition) |
| 12 | 140 | 60 | — | 210–211 |
| 13 | 135 | 60 | — | 189–192 |
| 14 | 125 | 20 | — | 173–176 |
| 15 | 125 | 20 | — | 196–198 |
| 16 | 135 | 30 | — | 204–208 |
| 17 | 130 | 7 | — | 97–99 |
| 18 | 130 | 10 | — | 109–112 |
| 19 | 130 | 10 | — | 120[a] |
| 20 | 95 | 5 | — | 248–250 |
| 21 | 130 | 5 | — | 224–229 |
| 22 | 130 | 4 | — | 273–276 |
| 23 | 130 | 60 | — | 228–231 |
| 24 | 140 | 5 | — | 193–198.5 |
| 25 | 130 | 5 | — | 233–234 |
| 26 | 195 | 10 | DIE[b] | 239.5–244 |
| 27 | 180 | 5 | nitrobenzene | 239–243 |
| 28 | 170 | 5 | — | 202–204.5 |
| 29 | 160 | 5 | — | 186–190 |
| 30 | 150 | 5 | — | 203–206.5 |
| 31 | 160 | 5 | — | 101–103 |
| 32 | 160 | 5 | — | 109.5–110.5 |
| 33 | 140 | 20 | nitrobenzene | Not crystalline |
| 34 | 150 | 1 | — | 98–100 |
| 35 | 160 | 15 | — | 131–134 |
| 36 | 130 | 15 | DIE | 157–160 |
| 37 | 140 | 30 | DIE | 168–171 |
| 38 | 130 | 30 | DIE | 150–152 |
| 39 | 130 | 30 | DIE | 166–168 |
| 40 | 140 | 30 | DIE | 68–69 |
| 41 | 140 | 30 | DIE | 167–169 |
| 42 | 130 | 30 | DIE | 158–160 |
| 43 | 130 | 30 | DIE | 123–125 |
| 44 | 130 | 30 | DIE | 167–170 |
| 45 | 130 | 60 | DIE | 62–64 |
| 46 | 140 | 30 | DIE | 171–174 |
| 47 | 130 | 30 | DIE | 89–92 |
| 48 | 160 | 30 | DIE | 167–168 |
| 49 | 165 | 30 | DIE | 174–176 |
| 50 | 160 | 60 | DIE | 59–61 |

[a]approximate m.p., compound very hygroscopic.
[b]DIE= di-isopropylethylamine.

Certain of the un-quaternised pyridines, wherein A$^3$ is an amide containing linkage, used as starting materials for the above compounds are novel, and may be obtained by the following process which exemplifies the preparation of the un-quaternised pyridine starting material for compounds 40 and 41:

Nicotinoyl chloride (14.15g.) was added over ten minutes, with stirring and cooling in an ice bath, to a solution of 3-amino-methylpyridine (10.8g.) and triethylamine (10.1g.) in methylene chloride (50ml.). After the addition was complete, the mixture was stirred at room temperature for an hour, diluted with water (100ml.), and the product was isolated from the organic phase by evaporation of the solvent. The crude product was recrystallised from ethyl acetate, m.p. 104°–106°C.

The following starting materials were prepared similarly, using the appropriate acid chlorides and amino compounds:

| Starting material for compounds nos. | M.p.(°C.) |
|---|---|
| 27 | 290–292 |
| 28 | 236–238 |
| 29, 30 | 232–235 |
| 31, 32 | 161–164 |
| 34 | 196–200.5 |
| 35 | 184–185.5 |
| 38, 39 | 163–166 |
| 40, 41 | 104–106 |
| 42, 43 | 75–78 |
| 44, 45 | 78–80 |
| 46, 47 | 83–85 |

The unquaternised pyridine starting material for compound 32 is also a novel compound and may be prepared as follows:

3-Aminomethylpyridine (10.8g.) and diphenyl carbonate (10.7g.) were mixed, heated together at 140°C. for 5 minutes, and the mixture was cooled and stirred with ether. The product was filtered off, washed with fresh ether, and recrystallised from ethyl acetate, m.p. 130.5°–133.5°C.

EXAMPLE 2

The process described in Example 1 is repeated, using the appropriate bis-pyridine derivatives and quaternising agents, to give the following compounds:

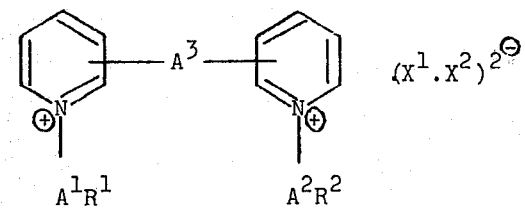

| No. | $A^1=A^2$ | $R^1=R^2$ | First linkage[a] | $A^{3[b]}$ | Second linkage[c] | $X^1=X^2$ |
|---|---|---|---|---|---|---|
| 51 | —CH₂CO.NH—[d] | n-octyl | 4 | —CH₂.CH₂— | 4 | Cl |
| 52 | —CH₂CO.NH— | n-decyl | 4 | —CH₂.CH₂— | 4 | Cl |
| 53 | — | n-nonyl | 4 | —CH:CH— | 4 | Ms[e] |
| 54 | — | 3,5,5-trimethylhexyl | 4 | —CH:CH— | 4 | Ms |
| 55 | — | n-decyl | 4 | —CO.NHNH.CO(CH₂)₄—CO.NHNH.CO— | 4 | Ms |
| 56 | — | n-decyl | 3 | —CO.N⟨⟩N.CO— | 3 | Ms |
| 57 | —CH₂CO.NH— | n-octyl | 3 | —CO.N⟨⟩N.CO— | 3 | Cl |
| 58 | —CH₂CO.NH— | n-decyl | 3 | —CO.N⟨⟩N.CO— | 3 | Cl |
| 59 | —CH₂CO.NH— | n-dodecyl | 3 | —CO.N⟨⟩N.CO— | 3 | Cl |
| 60 | — | n-decyl | 3 | —CO.NHNH.CO— | 3 | Ms |
| 61 | — | n-decyl | 3 | —CO.NH(CH₂)₄NH.CO— | 3 | Ms |
| 62 | — | n-decyl | 3 | —CO.NH—⟨⟩—NH.CO— (ortho) | 3 | Ms |
| 63 | — | n-decyl | 3 | —CO.NH—⟨⟩—NH.CO— | 3 | Ms |
| 64 | — | n-decyl | 3 | —NH.CO—⟨⟩—CO.NH— | 3 | Ms |
| 65 | — | n-decyl | 3 | —NH.CO.NH(CH₂)₃NH.—CO.NH— | 3 | Ms |
| 66 | — | n-decyl | 3 | —NH.CO.NH(CH₂)₄NH.—CO.NH— | 3 | Ms |
| 67 | — | n-decyl | 3 | —NH.CO.NH(CH₂)₆NH.—CO.NH— | 3 | Br |
| 68 | — | n-decyl | 3 | —CH₂NH.CO.NH(CH₂)₆—NH.CO.NHCH₂— | 3 | Br |
| 69 | — | n-nonyl | 3 | —NH.CO.NH— | 3 | Ms |
| 70 | — | n-decyl | 4 | —NH.CO.NH— | 4 | Ms |
| 71 | — | undec-10-enyl | 3 | —NH.CO.NH— | 3 | Ms |
| 72 | —CH₂CO.NH— | n-octyl | 3 | —NH.CO.NH— | 3 | Cl |
| 73 | —CH₂CO.NH— | n-decyl | 3 | —NH.CO.NH— | 3 | Cl |
| 74 | —CH₂CO.NH— | n-dodecyl | 3 | —NH.CO.NH— | 3 | Cl |
| 75 | — | n-decyl | 3 | —NH.CO.NHCH₂— | 3 | Ms |
| 76 | — | n-decyl | 3 | —NH.CO.NHCH₂— | 4 | Ms |
| 77 | — | n-decyl | 3 | —NH.COCH₂CO.NH— | 3 | Ms |
| 78 | — | n-decyl | 3 | —NH.CO(CH₂)₃CO.NH— | 3 | Cl |
| 79 | — | n-decyl | 3 | —NH.CO(CH₂)₃CO.NH— | 3 | Ms |
| 80 | — | n-nonyl | 3 | —NH.CO(CH₂)₄CO.NH— | 3 | Ms |
| 81 | — | 2-hexyloxyethyl | 3 | —NH.CO(CH₂)₄CO.NH— | 3 | Ms |
| 82 | — | n-decyl | 4 | —NH.CO(CH₂)₄CO.NH— | 4 | Ms |
| 83 | —CH₂CO.NH— | n-octyl | 3 | —NH.CO(CH₂)₄CO.NH— | 3 | Cl |
| 84 | — | undec-10-enyl | 3 | —NH.CO(CH₂)₄CO.NH— | 3 | Ms |
| 85 | —CH₂CO.NH— | n-decyl | 3 | —NH.CO(CH₂)₄CO.NH— | 3 | Cl |
| 86 | — | n-decyl | 3 | —NH.CO(CH₂)₅CO.NH— | 3 | Cl |
| 87 | — | n-decyl | 3 | —NH.CO(CH₂)₆CO.NH— | 3 | Cl |
| 88 | — | n-decyl | 3 | —NH.CO(CH₂)₆CO.NH— | 3 | Ms |
| 89 | — | n-decyl | 4 | —NH.CO(CH₂)₆CO.NH— | 4 | Ms |
| 90 | — | n-decyl | 3 | —NH.CO(CH₂)₇CO.NH— | 3 | Ms |
| 91 | — | n-decyl | 2 | —NH.CO(CH₂)₈CO.NH— | 2 | Ms |
| 92 | — | 2-(2-butoxyethoxy)-ethyl | 3 | —NH.CO(CH₂)₈CO.NH— | 3 | Ms |
| 93 | — | n-decyl | 4 | —CH₂NH.CO(CH₂)₂CO.—NHCH₂— | 4 | Ms |

-continued

| No. | A¹=A² | R¹=R² | First linkage[a] | A³[b] | Second linkage[c] | X¹=X² |
|---|---|---|---|---|---|---|
| 94 | — | n-decyl | 3 | —NH.COO(CH₂)₂OCO.NH— | 3 | Ms |
| 95 | — | n-decyl | 3 | —NH.COO(CH₂)₃OCO.NH— | 3 | Ms |
| 96 | — | n-decyl | 3 | —NH.COO(CH₂)₆OCO.NH— | 3 | Ms |
| 97 | — | n-decyl | 3 | —NH.COOCH₂C(C₂H₅)₂CH₂—OCO.NH— | 3 | Ms |
| 98 | — | n-decyl | 3 | —NH.CO[O(CH₂)₂]₂ OCO.—NH— | 3 | Ms |
| 99 | — | 3,5,5-trimethyl-hexyl | 3 | —NH.CO— | 4 | Ms |

[a] linkage of left hand pyridine ring to A³ in the formula as written at the head of the table.
[b] where A³ is not symmetrical, it should be read as from left to right in the formula at the head of the table.
[c] linkage of A³ to the right hand pyridine ring in the formula as written at the head of the table.
[d] the methylene group is attached to the pyridine nitrogen atom, and the NH group is attached to R.
[e] Ms=methanesulphonate.

| No. | Reaction conditions Temperature (°C.) | Time (minutes) | Additive | M.p. (°C.) |
|---|---|---|---|---|
| 51 | 110 | 15 | — | 237–239 |
| 52 | 110 | 15 | — | 261–266 |
| 53 | 140 | 10 | — | 255 |
| 54 | 125 | 20 | — | 200–250 |
| 55 | 160 | 30 | — | 165–168 |
| 56 | 130 | 10 | — | 212–214 |
| 57 | 120 | 20 | — | 238–239.5 |
| 58 | 110 | 30 | toluene | 229–231 |
| 59 | 110 | 30 | toluene | 224–228 |
| 60 | 175 | 5 | — | 168–171 |
| 61 | 150 | 15 | — | 122–125 |
| 62 | 160 | 10 | — | 112–114.5 |
| 63 | 160 | 15 | — | 128–130 |
| 64 | 195 | 10 | — | 210.5–212.5 |
| 65 | 180 | 15 | — | 95–98 |
| 66 | 200 | 2 | — | 114–116 |
| 67 | 140 | 30 | — | 193–194 |
| 68 | 140 | 150 | — | 91–95 |
| 69 | 145 | 5 | — | 202–206 |
| 70 | 140 | 5 | — | 100–104 |
| 71 | 150 | 2 | — | 200–203.5 |
| 72 | 100 | 15 | — | 250–252 |
| 73 | 105 | 15 | — | 250–253 |
| 74 | 100 | 15 | — | 258–260 |
| 75 | 180 | 30 | — | 95–98 |
| 76 | 180 | 20 | — | 110–113 |
| 77 | 160 | 10 | — | 142–144.5 |
| 78 | 150 | 60 | sulpholane | 214.5–216.5 |
| 79 | 140 | 10 | — | 154–155 |
| 80 | 130 | 10 | — | 197–199 |
| 81 | 140 | 5 | — | 156–159 |
| 82 | 140 | 5 | — | 120–123 |
| 83 | 160 | 5 | — | 225–228 |
| 84 | 160 | 2 | — | 196.5–197.5 |
| 85 | 130 | 15 | — | 228–230 |
| 86 | 165 | 120 | sulpholane + DIE[a] | 116–120 |
| 87 | 150 | 60 | sulpholane | 213–214.5 |
| 88 | 140 | 5 | — | 93.5–94.5 |
| 89 | 140 | 10 | — | 83–85 |
| 90 | 140 | 10 | — | 90 |
| 91 | 190 | 15 | — | 134–136 |
| 92 | 150 | 15 | — | 72–74 |
| 93 | 155 | 5 | — | 197–199 |
| 94 | 180 | 10 | — | 162–166 |
| 95 | 180 | 30 | — | 97–99 |
| 96 | 140 | 10 | — | 137–139 |
| 97 | 155 | 10 | — | 134–137 |
| 98 | 145 | 15 | — | 110–112 |
| 99 | 140 | 30 | DIE | 90–93 |

A. Certain of the unquaternised pyridines, wherein A³ is an amide-containing linkage, used as starting materials for the above compounds are novel, and may be obtained from the reaction of an appropriate amine and an appropriate acid chloride by the process described in the latter part of Example 1.

| Starting material for compounds nos. | M.p. (°C.) |
|---|---|
| 55 | 275–278 |
| 58 | 198–199.5 |
| 62 | 160–163 |
| 63 | 301–303 |
| 64 | 304.5–308 |
| 70 | 189–191 |
| 77 | 221–224.5 |
| 78/79 | 190–192.5 |
| 82 | 280–281 |
| 86 | 206–208.5 |
| 87/88 | 171.5–173.5 |
| 89 | 199.5–201.5 |
| 90 | 158–160 |
| 91 | 133.5–135 |
| 93 | 139–141 |

B. Certain other of the unquaternised pyridines, wherein A³ is a ureido-containing linkage, used as starting materials for the preparation of the above compounds of the invention, are novel and may be obtained as follows:

A solution of hexamethylene di-isocyanate (1.68g.) in toluene (10ml.) was added to a solution of 3-aminopyridine (1.88g.) in toluene (18ml.) and the mixture was heated on a steam-bath for 10 minutes. The mixture was cooled, and the product was filtered off, washed with toluene and dried, to give 1,6-bis[3-(pyrid-3-yl)ureido]hexane, m.p. 197°–199°C., the starting material for compound 67.

In a similar manner, using 3-aminomethylpyridine in place of 3-aminopyridine, there was obtained the starting material for compound 68, 1,6-bis[3-(pyrid-3-ylmethyl)ureido]hexane, m.p. 223°–225°C.

C. Certain other of the unquaternised pyridines, wherein A³ is a ureido- or urethane-containing linkage, used as starting materials for the preparation of the above compounds of the invention, are novel and may be obtained as follows:

A solution of tetramethylene diamine (0.535g.) in toluene (10ml.) was added with stirring and cooling to a solution of 3-pyridyl isocyanate (1.46g.) in toluene (15ml.). The mixture was stirred until the reaction was complete, and the product was filtered off, washed with toluene and crystallised from ethanol to give 1,4-bis[3-(pyrid-3-yl)ureido] hexane, m.p. 218°–219°C., the starting material for compound 66.

In a similar manner, using the appropriate isocyanate and the appropriate amine, diamine or diol, the following starting materials were prepared:

| Starting material for compounds nos. | M.p. (°C.) |
|---|---|
| 65 | 198.5–199.5 |
| 75 | 160–161 |
| 76 | 183–184.5 |
| 94 | 191–192 |
| 95 | 189–190 |
| 96 | 167–169 |
| 97 | 183–185 |
| 98 | 142–144 |

EXAMPLE 3

The process described in Example 1 is repeated using the appropriate bis-pyridine derivates and quaternising agents, to give the following compounds:

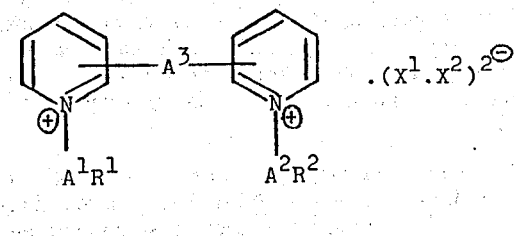

The unquaternised pyridine derivative used as starting material in the preparation of compound 109 may be obtained as follows:

Sodium hydride (1.32g.) was added portionwise under an atmosphere of nitrogen during 30 minutes, to a stirred solution of 3-hydroxypyridine (2.85g.) in dry dimethylsulphoxide (28ml.) cooled to below 25°C. When reaction ceased, 1,6-dibromohexane (3.66g.) was added dropwise with stirring and cooling, and the resulting mixture was stirred a further 3½ hours. The mixture was poured into ice-water, and the precipitated product was filtered off and crystallised from petroleum ether (b.p.60°–80°C.), to give 1,6-bis-pyrid-3-yloxyhexane, m.p. 85°C.

In a similar manner, using the appropriate dibromides, there were obtained the butane (m.p. 95°C.) and decane (m.p. 64°C.) analogues, the starting materials for compounds 108 and 110 respectively.

EXAMPLE 4

The methanesulphonate salt, compound 32 (3g.) was dissolved in water and excess 2N sodium hydroxide was added. A yellow viscous oil separated which was extracted into chloroform. The chloroform layer was washed with water, and then shaken with excess aqueous toluene-p-sulphonic acid. Ether was added to precipitate the toluene-p-sulphonate salt, which was crystallised from a mixture of acetone and acetonitrile, m.p. 127°–129°C.

The sulphate was prepared in similar manner, m.p. 146°–147°C.

The acetate (m.p. 87°–89°C.) was prepared in similar manner, except that the new salt remained in the aqueous phase and was recovered by evaporation of the solvent and crystallisation of the residue from acetone.

| No. | $A^1=A^2$ | $R^1=R^2$ | First linkage[a] | $A^{3[b]}$ | Second linkage[c] | $X^1=X^2$ |
|---|---|---|---|---|---|---|
| 100 | — | n-decyl | 3 | —NH.COCH=$^t$CHCO.NH— [d] | 3 | Ms[e] |
| 101 | — | n-octyl | 3 | —NH.CO(CH$_2$OCH$_2$)$_2$—CO.NH— | 3 | Br |
| 102 | — | n-decyl | 3 | —NH.COCH$_2$OCH$_2$CH$_2$—OCH$_2$CO.NH— | 3 | Br |
| 103 | — | n-decyl | 3 | —NH.CO[O(CH$_2$)$_2$]$_3$—OCO.NH— | 3 | Ms |
| 104 | — | n-decyl | 3 | —NH.COO(CH$_2$)$_2$NH.CO.—NH— | 3 | Ms |
| 105 | — | n-decyl | 2 | —NH(CH$_2$)$_2$NH— | 2 | Ms |
| 106 | — | n-decyl | 4 | —NH(CH$_2$)$_6$NH— | 4 | Br |
| 107 | — | n-decyl | 2 | —NH(CH$_2$)$_{10}$NH— | 2 | Ms |
| 108 | — | n-decyl | 3 | —O(CH$_2$)$_4$O— | 3 | Br |
| 109 | — | n-decyl | 3 | —O(CH$_2$)$_6$O— | 3 | Br |
| 110 | — | n-decyl | 3 | —O(CH$_2$)$_{10}$O— | 3 | Br |

[a]linkage of left hand pyridine ring to $A^3$ in the formula as written at the head of the table.
[b]where $A^3$ is not symmetrical, it should be read as from left to right in the formula at the head of the table.
[c]linkage of $A^3$ to the right hand pyridine ring in the formula as written at the head of the table.
[d]t indicates a trans double bond.
[e]Ms=methanesulphonate.

The unquaternised pyridine derivatives used as starting materials in the preparation of compounds 100 and 101 are novel, may be prepared by the process described in the latter part of Example 1, and have melting points of 321.5°–322.5°C. and 117°–119°C. respectively.

The unquaternised pyridine derivatives used as starting materials in the preparation of compounds 103 and 104 are novel, may be prepared by the process described at (C) in Example 2, and have melting points of 121°–123°C. and 194°–195.5°C. respectively.

EXAMPLE 5

Compositions containing a pyridine derivative of the invention may be prepared from any pyridine derivative of the invention described in the foregoing Examples by conventional procedures as illustrated below, where, it is to be understood, the particular pyridine derivative named may be replaced by an equipotent amount of any other pyridine derivative of the invention.

Lozenge

A mixture of sucrose (92.5g.), magnesium stearate (1g.), gum acacia (3g.), water (3ml.) and 3,3'- suberamidobis(1-n-decylpyridinium chloride) (0.5g.) is blended and compressed into hard lozenges such that each weighs 1g., and contains 5mg. of the antibacterial pyridine derivative.

Antiseptic 3,3'-Suberamidobis(1-n-decylpyridinium methanesulphonate) (0.5g.) is dissolved in sterile distilled water (99.5ml.) to give a liquid composition suitable for use as an antiseptic.

Toothpaste

A solution is prepared by stirring saccharin sodium (0.2g.) in purified water (38.8ml.) to which is then added isopropanol (4.0g.) and glycerin (20g.) (Solution I).

A mixture of oil of peppermint (0.6g.) and oil of spearmint (0.3g.) is added to Pluronic P75 (0.6g. — Pluronic is a trade mark) followed by 4,4'-glutaramidobis(1-n-decylpyridinium methanesulphonate) (0.5g.) and stirring is continued until a homogeneous solution is formed (Solution II).

Solution I is slowly added to Solution II, with stirring, and natrosol 250HH (1g. — Natrosol is a trade mark) is then added, stirring being continued until hydration is complete. A mixture of dicalcium phosphate (20g.), Neosyl E.T. (10g.), titanium dioxide (1g.) and dried aluminium hydroxide gel (1g.) is then added and mixing is continued until a smooth and uniform paste is formed.

What we claim is:

1. A pyridine derivative of the formula:

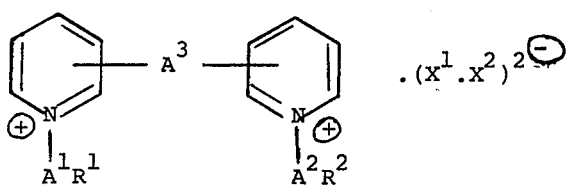

wherein $R^1$ and $R^2$ which may be the same or different are each alkyl having 8 to 14 carbon atoms, n-undec-10-yl, 2-n-hexyloxyethyl, 2-(2-butoxyethoxy)ethyl, 3,4-dichlorophenyl, 4-chlorobenzyl, 2,4-dichlorobenzyl or 2-naphthylmethyl; $A^1$ and $A^2$ are each a direct linkage or a linking group of the formula —CH$_2$CO.NH— wherein the methylene is joined to the pyridine nitrogen; $(X^1.X^2)^{2-}$ represents two monoanions or a dianion selected from the group consisting of two halide, methanesulphonate, toluene-p-sulphonate or acetate ions or the sulphate dianion; and $A^3$ is a linking group of the formula:

—(CH$_2$)$_n$NH.CO.NH(CH$_2$)$_y$NH.CO.NH(CH$_2$)$_n$— wherein $n$ is 0, 1 or 2; and $y$ is 0 or 2 to 6.

2. The pyridine derivative of claim 1 wherein $R^1$ and $R^2$ are the same and are each n-octyl, n-nonyl, n-decyl, n-undecyl, n-dodecyl, n-tetradecyl, n-undec-10-enyl, 2-n-hexyloxyethyl, 2-(2-butoxyethoxy)ethyl, 3,4-dichloro-phenyl, 4-chlorobenzyl, 2,4-dichlorobenzyl or 2-naphthylmethyl.

3. The pyridine derivative of claim 1 wherein $A^1$ and $A^2$ are each a direct linkage, $R^1$ and $R^2$ are each the same unbranched alkyl of 8 to 11 carbon atoms, $(X^1.X^2)^{2-}$ represents two bromide, chloride, methanesulphonate, toluene-p-sulphonate or acetate anions or the sulphate dianion, and $A^3$ is a linking group of the formula:

—NH.CO.NH(CH$_2$)$_{3-6}$NH.CO.NH—.

4. The pyridine derivative of claim 1 in which $R^1$ and $R^2$ are both n-decyl; $A^1$ and $A^2$ are each a direct linkage; $(X^1.X^2)^{2-}$ represents two methanesulphonate anions and $A^3$ is a linking group of the formula:

—NH.CO.NH(CH$_2$)$_3$NH.CO.NH— connected between the 3- positions of the pyridine rings.

5. The pyridine derivative of claim 1 in which $R^1$ and $R^2$ are both n-decyl; $A^1$ and $A^2$ are each a direct linkage; $(X^1.X^2)^{2-}$ represents two methanesulphonate anions and $A^3$ is a linking group of the formula:

—NH.CO.NH(CH$_2$)$_4$NH.CO.NH— connected between the 3- positions of the pyridine rings.

6. The pyridine derivative of claim 1 in which $R^1$ and $R^2$ are both n-decyl; $A^1$ and $A^2$ are each a direct linkage; $(X^1.X^2)^{2-}$ represents two bromide anions and $A^3$ is a linking group of the formula: —NH.CO.NH(CH$_2$)$_6$NH.CO.NH— connected between the 3- positions of the pyridine rings.

* * * * *